(12) United States Patent
Abraham et al.

(10) Patent No.: US 9,827,144 B2
(45) Date of Patent: Nov. 28, 2017

(54) METHOD FOR TESTING A LASER DEVICE

(71) Applicant: Novartis AG, Basel (CH)

(72) Inventors: Mario Abraham, Burgthann (DE); Peter Riedel, Erlangen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/248,977

(22) Filed: Aug. 26, 2016

(65) Prior Publication Data
US 2017/0143542 A1    May 25, 2017

(30) Foreign Application Priority Data
Nov. 20, 2015   (DE) .................. 10 2015 015 095

(51) Int. Cl.
| | | |
|---|---|---|
| *G01B 9/00* | (2006.01) | |
| *A61F 9/008* | (2006.01) | |
| *G01N 21/84* | (2006.01) | |

(52) U.S. Cl.
CPC ...... *A61F 9/00802* (2013.01); *A61F 9/00825* (2013.01); *G01N 21/84* (2013.01); *A61F 2009/00846* (2013.01); *A61F 2009/00855* (2013.01); *A61F 2009/00859* (2013.01); *A61F 2009/00872* (2013.01); *G01N 2201/06113* (2013.01)

(58) Field of Classification Search
CPC .......... G01N 2021/8416; G01N 21/84; G01N 21/6456; G01N 21/718; G01N 2021/0346; G01N 2021/0357; G01N 2021/1793; G01N 2021/637; G01N 2021/655; G01N 21/03; G01N 21/45; G01N 21/4795; G01N 21/6452

See application file for complete search history.

(56) References Cited

U.S. PATENT DOCUMENTS

| | | | |
|---|---|---|---|
| 2,673,984 A | | 4/1954 | Clarke |
| 4,272,190 A | * | 6/1981 | Shapiro .............. G01M 11/0235 356/124 |
| 6,129,722 A | * | 10/2000 | Ruiz ........................ A61F 9/008 351/212 |

(Continued)

FOREIGN PATENT DOCUMENTS

DE    102009006306 A1    7/2010

OTHER PUBLICATIONS

Dorronsoro et al.; "Experimental evaluation of optimized ablation patterns for laser refractive surgery"; Optical Society of America; Aug. 17, 2009; pp. 15292-15307; vol. 17, No. 17; Optics Express.

(Continued)

*Primary Examiner* — Michael P Stafira

(57) ABSTRACT

A method for testing a laser device configured to emit pulsed, focused laser radiation includes providing an artificial eye body with a pattern that simulates a pupil and/or an iris structure. An irradiation test object is arranged above the pattern. The irradiation test object is separate from the eye body and is made of a material that is modifiable by the laser radiation. The laser radiation is applied to the irradiation test object according to a predefined application profile, so that a material modification that corresponds to the application profile is generated in the irradiation test object.

17 Claims, 2 Drawing Sheets

(56) References Cited

U.S. PATENT DOCUMENTS

2004/0260275 A1* 12/2004 Liang .................. A61B 3/1015
  606/5
2005/0131398 A1   6/2005 Campbell et al.
2012/0080586 A1   4/2012 Deisinger et al.

OTHER PUBLICATIONS

Taylor et al.; "Determining the Accuracy of an Eye Tracking System for Laser Refractive Surgery"; Journal of Refractive Surgery; Sep./Oct. 2000; pp. S643-S646; vol. 16; Centre for Ophthalmology and Visual Science, Nedlands, Australia.

* cited by examiner

METHOD FOR TESTING A LASER DEVICE

CROSS REFERENCE TO RELATED APPLICATIONS

This application claims priority to German Patent Application Serial Number 102015015095.2, filed 20 Nov. 2015, titled "METHOD FOR TESTING A LASER DEVICE," which is hereby incorporated by reference in its entirety.

TECHNICAL FIELD

The present disclosure relates in general to the testing of a laser device which is configured for emitting pulsed, focused laser radiation. The present disclosure relates in particular to a method for visualizing an application profile of the laser radiation in an irradiation test object.

BACKGROUND

Pulsed laser radiation is used in the refractive laser treatment of a human eye, for example for making cuts in the cornea or for the ablation of corneal tissue (i.e., for removing tissue from the corneal surface). The irradiated laser radiation causes a photodisruptive process in the corneal tissue, which results in tissue separation or vaporization of tissue. Within the scope of such treatment of the cornea, the corneal surface is re-formed, thus altering the refractive property of the cornea in order to reduce or completely eliminate vision defects of the eye.

Test applications are typically carried out prior to the actual laser treatment of the human eye. In this case, the laser radiation is applied to a test object according to an example application profile. Such test applications are used, for example, for calibrating the laser device used for the laser treatment, such as for calibrating the energy of the laser radiation that is emitted by the laser device. For testing the ablation caused by the laser radiation, the laser radiation is conventionally directed onto photographic paper, and the material removal which occurred on the photographic paper is determined.

In the course of a laser treatment, the eye to be treated typically moves translationally and rotationally in multiple dimensions. Eye tracking systems (so-called eye trackers) having at least one infrared camera are used to record infrared images of the eye, and by means of suitable processing software, to detect from the recorded infrared images the movement of the eye in the course of treatment. To simulate the application of the laser radiation which is adapted to the eye movement of a patient, the test objects have eye structures, for example an eye pupil and an iris structure, which are detectable using the eye tracking system. These types of test objects are conventionally realized as sheet- or plate-shaped objects having an imprinted replica of at least one of the eye structures. However, within the scope of test applications, all degrees of freedom of the eye movement which are possible in the course of treatment, for example a rotational eye movement, cannot be adequately simulated using the described test objects.

SUMMARY OF EXEMPLARY EMBODIMENTS

It is an object of the present invention to provide a method for testing a laser device which is configured for emitting pulsed, focused laser radiation, according to which test applications of various types may be implemented.

One aspect of the present invention is a method for testing a laser device which is configured for emitting pulsed, focused laser radiation. The method comprises providing an eye body which bears a pattern that includes (for example, simulates) a pupil and/or an iris structure, and arranging an irradiation test object, which is separate from the eye body and which is made of a material which is modifiable by the laser radiation of the laser device, above the pattern. The method further comprises applying laser radiation of the laser device to the irradiation test object according to a predefined application profile, so that a material modification which corresponds to the application profile is generated in the irradiation test object.

The material modification that is generated in the irradiation test object allows a visualization of the profile of the applied laser radiation. The application profile may correspond to an example test profile (for example, for calibrating the laser device), or also to an example treatment profile or patient-specific treatment profile, as is carried out within the scope of a refractive laser treatment of a real eye. Thus, it may be provided that the method also comprises computing a (patient-specific) corneal ablation profile based on diagnostic data of a real eye, and using the ablation profile or a profile derived therefrom as an application profile in the step of applying the laser radiation.

In one embodiment, the irradiation test object has a design as a shell (or bowl), and is situated with its concave shell bottom side facing the pattern. The material modification produced in the irradiation test object may then include an ablation from the convexly curved shell top side. The shell top side, at least in the state in which it is situated on the pattern, may extend along two convex lines of curvature running crosswise with respect to one another. The curvature of the shell top side may, for example, simulate the curvature of a human corneal surface.

In certain embodiments, the irradiation test object is removably situated above the pattern, for example, placed on the eye body. In this case, the irradiation test object which is modified (by the application of the laser radiation) is removed from the eye body and selectively replaced by an unmodified irradiation test object. In addition, the modified irradiation test object may be used separately from the eye body for further visualization and/or analysis of the material modification that has been generated, or of the predefined application profile.

The irradiation test object may be designed as a hard shell or as a soft shell. It may be provided that the shape (and diameter) of the hard shell does not significantly change, even after the irradiation test object is removed from the eye body. In addition, it may be provided that the shell shape, for example the convex curvature, of the soft shell changes, for example flattens, at least after the irradiation test object is removed from the eye body. In this case, a shell diameter may become greater as a function of the flattening.

The irradiation test object covers at least a portion of the pattern. Thus, for example, it may be provided that the irradiation test object covers only a portion of a pattern, including the eye pupil and the iris structure, which contains the eye pupil. In certain embodiments, however, the irradiation test object is dimensioned in such a way that it completely covers the pattern. The irradiation test object may have a shell diameter of between approximately 8 mm and approximately 16 mm, in particular between approximately 10 mm and approximately 13 mm.

It may be provided that the irradiation test object is placed on the eye body with a space between the shell bottom side and the pattern. At least in this case, the eye body may have a flattened area in the region of the pattern, and the irradiation test object may be situated above the flattened area. For example, the irradiation test object may be pulled over an annular edge surrounding the flattened area.

Alternatively, it may be provided that the irradiation test object is situated on the eye body without a space between the shell bottom side and the pattern. It may be provided, for example, that the irradiation test object is pulled over a convexly curved surface of the eye body, for example in the form of a spherical surface.

The eye body may be an artificial eye body. In this case, the pattern may simulate the pupil and/or the iris structure. Alternatively, the eye body may be the eye body of a human eye including a pupil and an iris structure.

According to one embodiment, the material modification which is produced as a function of the application profile includes a discoloration and/or a removal of material from the irradiation test object. At least in this case, the irradiation test object may be a solid body. It may be provided, for example, that the irradiation test object is made of a plastic material. According to an alternative embodiment, the material of the irradiation test object includes a liquid material which is solidifiable by the applied laser radiation. In this case, the material modification may include a solidification of material in the irradiation test object. For example, a three-dimensional model which simulates the application profile may be solidified in the liquid material.

In certain embodiments, the irradiation test object is permeable at least to light in the infrared wavelength range. At least in this case, it may be provided that the method further comprises recording of images at least of a portion of the pattern of the eye body through the irradiation test object, using at least one camera, in particular an infrared camera. The camera may be, for example, part of a provided eye tracking system (an eye tracker, for example).

It may be provided that the method further comprises determining a position and/or an orientation of an eye reference feature (for example, at least one eye structure), based on the recorded images. A movement of the eye body relative to the camera may be detected based on a plurality of determined positions and/or orientations of the eye reference feature. The detected movement of the eye body may include a translational movement and/or a rotational movement about at least one of the three spatial axes x, y, z relative to the camera. The laser radiation may be applied as a function of the determined position and/or orientation, or of the detected movement of the eye reference feature.

BRIEF DESCRIPTION OF THE DRAWINGS

Supplemental features, advantages, and components of the present invention are apparent from the following description of the appended drawings, in which.

DETAILED DESCRIPTION OF EXEMPLARY EMBODIMENTS

Figure 1:
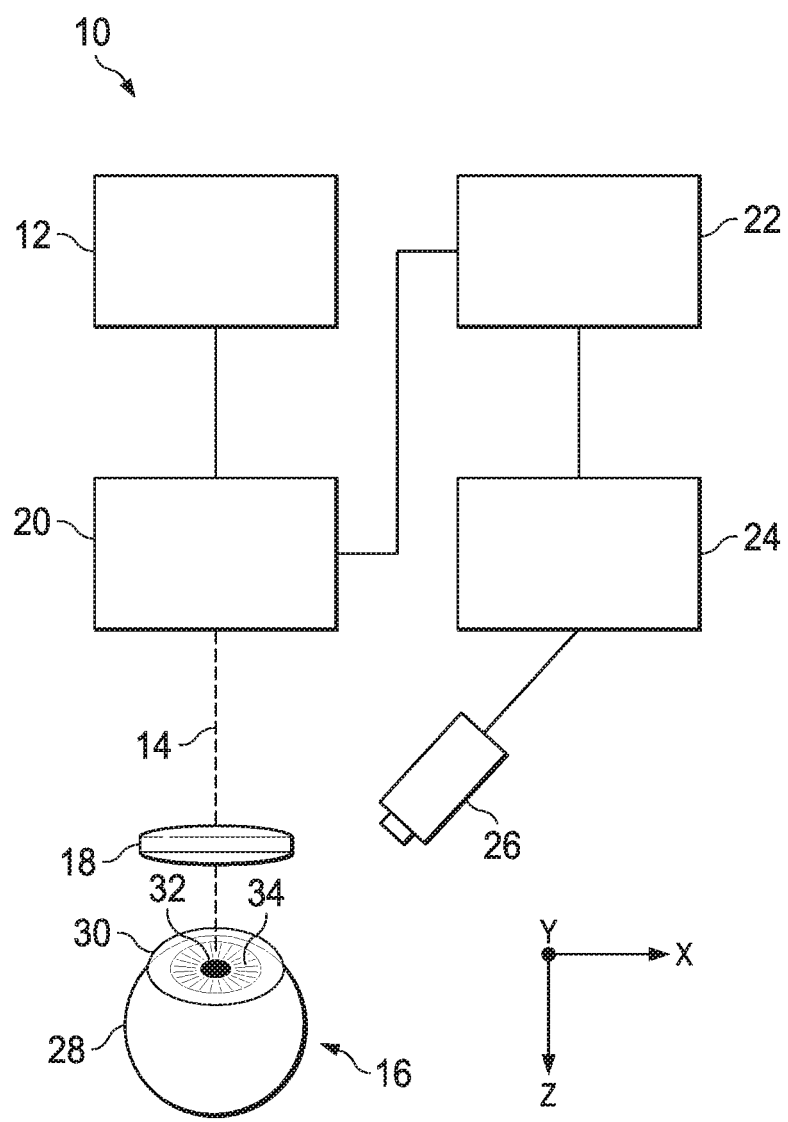
FIG. 1 shows one exemplary embodiment of a laser device for treatment of an irradiation test object on an eye body.

FIG. 1 shows a highly schematic illustration of one exemplary embodiment of a laser device, denoted in general by reference numeral 10, for the refractive laser treatment of a human eye. The laser device 10 includes a laser source 12 which generates pulsed laser radiation that is suitable for the eye treatment. For ablative treatments, the wavelength of the laser radiation generated by the laser source 12 is in the UV range. For example, the laser source 12 includes a 193 nm excimer laser.

The laser radiation generated by the laser source 12 propagates along an optical beam path 14 (designated as the z-direction), and then strikes an eye model 16. In the exemplary embodiment shown in FIG. 1, this is an artificial eye model 16, as described in greater detail below. In the case of a real application, the eye model 16 may instead be provided by a real eye of a patient to be treated.

Various components for guiding and shaping the laser radiation may be situated in the beam path 14. In the exemplary embodiment shown in FIG. 1, these components include in particular a focusing objective 18 and a scanner 20, connected upstream from the focusing objective 18, by means of which the focus of the laser radiation provided by the laser source 12 and produced by the focusing objective 18 is deflectable in the z-direction and transversely with respect to the beam path (in the x- and y-directions).

The laser device 10 also includes a control system 22 which controls the scanner 20 according to a predefined control program. The control program implements, for example, an application profile to be generated in the eye model 16, in particular an ablation profile to be generated. The application profile may correspond to a profile of a test application, as is carried out, for example, within the scope of a calibration of the laser device 10, for example the laser source 12 and/or the scanner 20. For this purpose, for example the energy of the generated laser radiation may be varied within a plurality of successive application steps. Alternatively or additionally, the application profile may correspond to an ablation profile of an example laser treatment or patient-specific laser treatment. It may be provided, for example, to compute an ablation profile based on diagnostic data of a real eye, and to implement this ablation profile or a profile derived therefrom as the application profile.

It may also be provided that the laser source 12 is designed as an ultrashort pulse laser which emits pulsed laser radiation with pulse durations in the range of picoseconds, femtoseconds, or attoseconds and which is suitable for cutting within eye tissue, as is necessary, for example, for laser in situ keratomileusis (LASIK) or in cataract surgery.

FIG. 1 shows an eye tracking system 24, indicated in a highly schematic fashion. The eye tracking system 24 may be an eye tracker which is designed to detect a translational and a rotational eye movement in multiple dimensions, in particular in more than two dimensions. The eye tracker 24 may be provided as part of the laser device 10, or also in the form of a separate device.

The eye tracker 24 may be implemented in various ways known to those skilled in the art. In the exemplary embodiment shown in FIG. 1, the eye tracker 24 includes an infrared camera unit 26 which is configured for recording a plurality of infrared images of the eye model 16, for example using one or a plurality of infrared cameras positioned around the eye model 16. In another exemplary embodiment, the eye tracker may be realized as an eye tracker based on optical coherence tomography (OCT). The eye tracker 24 is configured for detecting the position and/or the orientation or movements of the eye model 16 based on the recorded infrared images. For this purpose, the eye tracker 24 may make use of suitable image recognition processes by means of which at least one eye reference feature, for example at least one eye structure (for example, an edge of an eye pupil and/or an iris structure), in the recorded infrared images is determined.

In the exemplary embodiment shown in FIG. 1, the eye tracker 24 is connected to the control system 22 of the laser device 10 via a suitable interface, so that the data collected by the eye tracker 24 may be relayed to the control system 22. The control system 22 is configured for controlling the laser radiation, taking into account the position and/or orientation of the eye model 16 determined by the eye tracker 24. Thus, it is provided to apply the laser radiation to the eye model 16 as a function of a movement of the eye reference feature, for example a beam focus position on the eye model 16, which is spatially adapted to a changing position and/or orientation of the eye reference feature.

The eye model 16 shown in FIG. 1 includes an artificial eye body 28 and an irradiation test object 30. A pattern is applied to the artificial eye body 28, which simulates an eye pupa 32 and an iris structure 34. The irradiation test object 30 is situated above the pattern, for example, completely covering or overlapping the pattern. The eye model 16 may undergo translational movements along the three spatial directions x, y, z, as well as rotational movements about the three spatial axes x, y, z (as illustrated by the coordinate system shown in FIG. 1) relative to the infrared camera unit 26 of the eye tracker 24.

It may be provided to dispose the eye model 16 (the eye body 28, for example) on a positioning device, not illustrated here. The positioning device may also be configured for causing a movement of the eye model 16. The positioning device may be situated, for example, in the area of a head support of a patient table (used within the scope of a refractive laser treatment), for example by insertion into the patient table by means of a simple form-locked fit. Alternatively or additionally, the relative movement between the eye tracker 24 and the eye model 16 may take place, for example, by changing the position and orientation of the infrared camera unit 26.

In another exemplary embodiment, the eye model 16 may include the irradiation test object 30 which is situated on a human eye of a patient. In this case, no artificial eye body 28 is necessary. Similar to the above embodiment including an artificial eye body 28, the irradiation test object 30 is situated above the pattern, for example, completely covering or overlapping the pattern (for example, such as a contact lens). The pattern is formed by the pupil and/or the iris structure of the human eye.

Figure 2A:
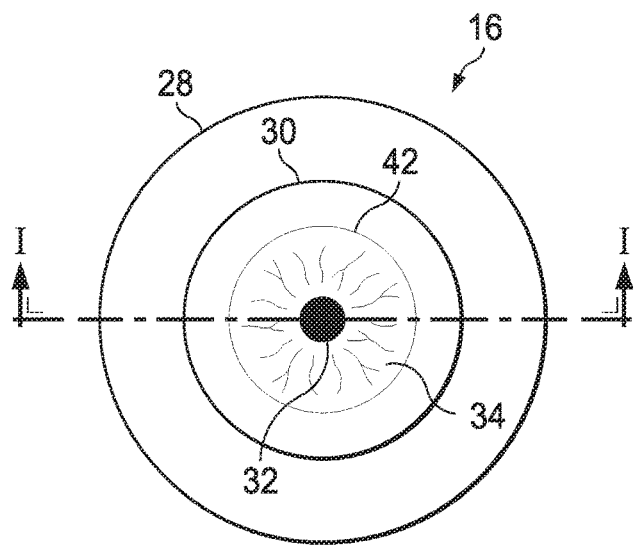
FIGS. 2A through 2C show one exemplary embodiment of an artificial eye body and of the irradiation test object.
Figure 2B:
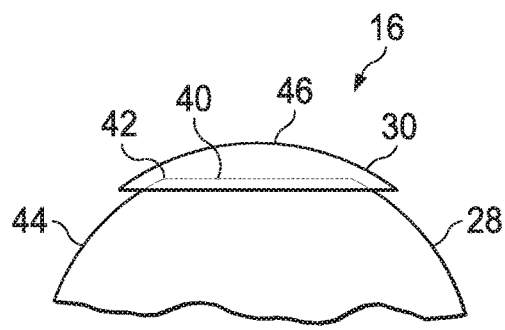
Figure 2C:
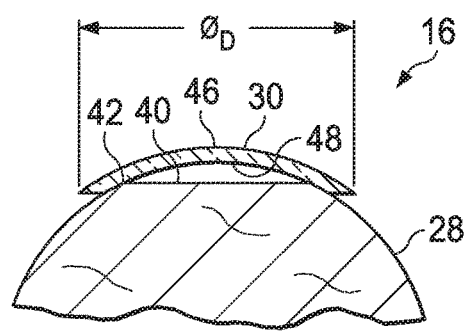

FIGS. 2A through 2C show schematic illustrations of one exemplary embodiment of the eye model 16 from FIG. 1. FIG. 2A shows a top view. FIG. 2B shows a side view, and FIG. 2C shows a sectional view of the eye model 16 along the section line I indicated in FIG. 2A.

The eye model 16 includes the artificial eye body 28 and the irradiation test object 30, as already described with reference to FIG. 1. In the exemplary embodiment shown in FIGS. 2A through 2C, the eye body 28 has a flattened area 40 within which the surface of the eye body 28 is planar. The flattened area 40 forms a disk-shaped (for example, an ellipsoidal, and in particular circular) cover surface of the eye body 28. A convexly curved peripheral surface 44 which surrounds the flattened area 40 in a ring-like manner is joined to the flattened area 40 via an annular, e.g. circular, edge 42. The peripheral surface 44 is designed as an annular surface in accordance with the shape of an ellipsoidal surface (for example, a spherical surface). The eye body 28 may assume, for example, the shape of an ellipsoidal disk (for example, a spherical disk) or an ellipsoidal surface (for example, a spherical surface).

In the region of the flattened area 40, the eye body 28 bears the pattern having the simulation (i.e., replica) of the eye pupil 32 and the iris structure 34 (see FIG. 1). The pattern contrasts in color with the peripheral surface 44 of the eye body 28, even under infrared illumination. In the exemplary embodiment shown in FIGS. 2A through 2C, the pattern extends over the entire flattened area 40 of the eye body 28. In another exemplary embodiment, it may be provided that the pattern simulates only the iris structure 34 or only the eye pupil 32. At least in this case, the eye model 16 may bear no pattern in a region of the flattened area 40 (for example, in the case of only a pupil simulation, in an area around the eye pupil 32). In such an area, it may be provided not to apply (to print or to glue, for example) a pattern to the eye body 28.

The irradiation test object 30 is situated on the eye body 28, specifically, above the pattern which the eye body 28 bears. In the exemplary embodiment shown in FIGS. 1 through 2C, the irradiation test object 30 situated on the eye body 28 has a shell shape (also referred to below as a test shell 30).

The test shell 30 has a convexly curved shell top side 46. It may be provided that the shell top side 46 has an approximately bitoroidal shape. Thus, the shell top side 46 may extend along two lines of curvature, running crosswise with respect to one another, in an aspherical manner in each case, with different respective radii of curvature. At least in this case, the convex curvature of the shell top side 46 may substantially correspond to the curvature of a human corneal surface.

The test shell 30 also has a concavely curved shell bottom side 48, opposite from the shell top side 46, as is apparent in FIG. 2C. In the state of the test shell 30 in which it is situated on the eye body 28, the shell bottom side 48 faces the pattern. It may be provided that a thickness of the test shell 30 extending between the shell bottom side 48 and the shell top side 46 has no significant variation, at least within the area situated above the pattern. It may be further provided that the thickness of the test shell takes values between about 200 μm and about 1000 μm, such as between about 400 μm and about 700 μm.

The test shell 30 is placed on the eye body 28. For this purpose, the test shell 30 in the exemplary embodiment shown in FIGS. 1 through 2C is pulled over the annular edge 42 which surrounds the flattened area 40 of the eye body 28, for example in the manner of a dome which covers the flattened area 40. Alternatively, it may be provided, for example, to situate the test shell 30 on the flattened area 40 of the eye body 28 (for example, to place it on the flattened area 40, or to insert it into grooves introduced into the flattened area 40).

It is also conceivable for the eye body 28 to have a convexly curved surface, such as a surface which conforms to a spherical surface, for example, also in the area of the pattern or a portion of the pattern (for example, in the area of the simulation of the iris structure 34). In this case, the irradiation test object 30 may be pulled, for example, over the convexly curved surface region of the eye body 28 which bears the pattern. In this case, the shell bottom side 48 may fit closely against the convexly curved surface of the eye body 28.

In the exemplary embodiment shown in FIGS. 1 through 2C, in particular a shell diameter $Ø_D$ between approximately 10 mm and 13 mm is provided for the test shell 30 (see FIG. 2C). The shell diameter describes the diameter of a ring that is formed by the edge of the shell bottom side 48. Alternatively, the test shell 30 may have a larger or smaller diameter between approximately 8 mm and 16 mm. The dimensioning of the shell diameter may depend, for example, on the pattern to be covered by the test shell 30. Thus, in the case of covering only the simulation of the eye pupa 32, a smaller shell diameter may be provided compared to the case of covering at least a simulation of an iris structure 34. In addition, the magnitude of the shell diameter may be such that the test shell 30 is insertable into a real eye.

In certain embodiments, the test shell 30 is designed as a hard shell. In this case, the test shell 30 has substantially the same shell curvature and the same shell diameter, whether it is removed from the eye body 28 or is situated on the eye body 28. Alternatively, however, the test shell 30 may also be designed as a soft shell. It may be provided, for example, that the shell curvature of the test shell 30 is flattened when the test shell 30 is removed from the eye body 28, and the shell diameter becomes larger as a function of the flattening. In this case, the shell diameter $\varnothing_D$ shown in FIG. 2C is understood as the shell diameter of the test shell 30 on the eye body 28. For example, a soft shell may be used in the case of intrastomal operations.

As indicated in FIGS. 1 and 2A, the irradiation test object 30 is designed to be permeable at least to light of a predefined wavelength range. Within the scope of use of the eye model 16 with the eye tracker 24 described for FIG. 1, it may be provided that the irradiation test object 30 is made of a material which is permeable in particular to light in the infrared wavelength range. A space between the surface of the eye body 28 bearing the pattern and the shell bottom side 46 of the irradiation test object 30 may also be filled with air or some other medium which is permeable to light, at least in the infrared wavelength range. It may thus be provided to record infrared images of the pattern of the eye body 28 situated beneath the irradiation test object 30, using the infrared camera unit 26 of the eye tracker 24. In certain embodiments, the irradiation test object 30 is also designed in such a way that the pattern which is detectable through the irradiation test object 30 has no significant optical distortion.

The irradiation test object 30 shown in FIGS. 1 through 2C is also made of a material that is modifiable by the laser radiation of the laser device 10 described with reference to FIG. 1, so that a material modification which visualizes the application profile results in the irradiation test object 30 by applying laser radiation according to a predefined application profile.

In the exemplary embodiment shown in FIGS. 1 through 2C, the material modification includes a removal of material from the surface of the irradiation test object 30 in the area of the beam focus. Specifically, material is removed (vaporized) from the shell top side of the test shell 30, for example within the scope of ablation of a human cornea. The material modification may also include a discoloration of the irradiation test object 30. The discoloration of the irradiation test object 30 may be, for example, that the material of the irradiation test object 30 turns a milky color, for example on the shell top side 46 of the test shell 30 in the area of a beam focus of the applied laser radiation. In another exemplary embodiment, the material modification may include a coloration of the irradiation test object (such as a change of color in dependence of varying corneal depths of the application profile).

The irradiation test object 30 is provided as a solid body made of a solid material. The solid body is dimensionally stable, for example with a rigid or flexible design. Alternatively, the solid body (in the case of the soft shell, for example) may be dimensionally unstable, for example with an elastic design. The solid material may include a plastic material (such as polymethylmethacrylate). It may also be provided to use a (hard or soft) contact lens (preferably without refractive correction) as the solid body. At least in this case, the material of solid body may, for example, include silicon hydrogel.

Alternatively, the material modification may include material solidification. It may be provided that the material of the irradiation test object 30 includes a liquid material which is solidifiable by the laser radiation of the laser device 10 (see FIG. 1). For example, a three-dimensional model which visualizes the application profile may be produced by the material solidification.

When the eye model 16 described with reference to FIGS. 1 through 2C is used with the laser device 10 shown in FIG. 1, the laser treatment of a human eye may be simulated by means of the laser device 10, with simultaneous eye tracking. The application profile may correspond to either an example treatment profile or a patient-specific treatment profile (ablation profile). In addition, a typical eye movement of a patient in the course of a refractive laser treatment may be simulated by a movement of the eye model 16 (caused by means of a positioning device, for example) and the detection of movement by means of the eye tracker 24. The material modification produced in the irradiation test object 30 then visualizes the result of such a treatment under actual conditions.

The modified irradiation test object 30 may be removed from the eye body 28, for example for analysis of the material modification. Thus, the material modification may be harmonized with the application profile implemented by the control program, for example for calibrating the laser device 10, for one or more function tests of the laser device 10 and/or the eye tracker 24, and/or for visualizing the laser treatment (for a patient, for example). It may be provided that the modified irradiation test object 30 is insertable into a real eye, for example to illustrate to a patient the effect of the material modification on the refractive property of the cornea. In addition, it may be provided to replace the modified irradiation test object in the laser device 10 with an unmodified irradiation test object 30 in order to repeat the application of the laser radiation according to the same application profile, or according to an altered application profile.

The features of the irradiation test object 30 have been described in connection with the artificial eye body 28. It is to be understood that the irradiation test object 30 as shown in FIGS. 1 to 2C may be instead used together with a real human eye of a patient. In this case, the patient is allowed to experience the course and the outcome (the change of the refractive property of the cornea) of the laser treatment.

The invention claimed is:

1. A method for testing a laser device configured to emit pulsed, focused laser radiation, the method comprising the following:
   providing an eye body having a pattern that includes a pupil or an iris structure;
   arranging an irradiation test object above the pattern, the irradiation test object being separate from the eye body and comprising a material that is modifiable by the laser radiation of the laser device;
   applying the laser radiation of the laser device to the irradiation test object according to a predefined application profile, so that a material modification corresponding to the application profile is generated in the irradiation test object.

2. The method according to claim 1, wherein:
the irradiation test object has a shell-shaped design, and
the irradiation test object is situated with its concave shell bottom side facing the pattern.

3. The method according to claim 1, wherein the material modification includes removal of material from the top side of the irradiation test object.

4. The method according to claim 2, wherein the irradiation test object is a hard shell.

5. The method according to claim 2, wherein the irradiation test object is a soft shell.

6. The method according to claim 1, wherein the irradiation test object is dimensioned in such a way that it completely covers the pattern.

7. The method according to claim 2, wherein the irradiation test object has a shell diameter of between approximately 8 mm and approximately 16 mm.

8. The method according to claim 2, wherein the irradiation test object is placed on the eye body with a space between the shell bottom side and the pattern.

9. The method according to claim 2, wherein the irradiation test object is situated on the eye body without a space between the shell bottom side and the pattern.

10. The method according to claim 1, wherein the eye body is an artificial eye body with a pattern that simulates the pupil or the iris structure.

11. The method according to claim 10, wherein:
the eye body has a flattened area in the region of the pattern, and
the irradiation test object is situated above the flattened area.

12. The method according to claim 1, wherein:
the irradiation test object is a solid body, and
the material modification includes a discoloration or a removal of material of the irradiation test object.

13. The method according to claim 1, wherein the irradiation test object is made of a plastic material.

14. The method according to claim 1, wherein:
the material of the irradiation test object includes a liquid material that is solidifiable by the applied laser radiation, and
the material modification includes a solidification of material of the irradiation test object.

15. The method according to claim 1, further comprising:
computing a patient-specific corneal ablation profile based on diagnostic data of a real eye; and
wherein the step of applying the laser radiation of the laser device comprises using the ablation profile or a profile derived therefrom as an application profile to apply the laser radiation.

16. The method according to claim 1, wherein the irradiation test object is permeable at least to light in the infrared wavelength range.

17. The method according to claim 1, further comprising:
recording a plurality of images of at least of a portion of the pattern of the eye body through the irradiation test object using an infrared camera; and
determining a position of an eye reference feature based on the recorded images,
wherein the step of applying the laser radiation of the laser device comprises applying the laser radiation as a function of the determined position of the eye reference feature.

* * * * *